United States Patent [19]

Anderson et al.

[11] Patent Number: 4,943,664
[45] Date of Patent: Jul. 24, 1990

[54] SURFACTANT PRODUCTS CONTAINING 1,3,4-BUTANETRIOL

[75] Inventors: Lowell R. Anderson, Morristown; Mohamed M. Hashem, Wayne; Robert B. Login, Oakland, all of N.J.

[73] Assignee: GAF Chemicals Corporation, Princeton, N.J.

[21] Appl. No.: 410,783

[22] Filed: Sep. 22, 1989

[51] Int. Cl.$^5$ .............................................. C07C 43/10
[52] U.S. Cl. .................................. 568/623; 564/507; 568/613
[58] Field of Search ................. 568/623, 613, 617, 680

[56] References Cited

U.S. PATENT DOCUMENTS 4,416,868 11/1983 Vanlerberghe et al. ............. 568/613
4,788,345 11/1988 Sebag et al. ......................... 568/623

FOREIGN PATENT DOCUMENTS 63-30491 2/1988 Japan .
1180591 2/1970 United Kingdom ................ 568/623

OTHER PUBLICATIONS

Miyazaki et al, "Preparation of Cyclourethane Containing, etc.", CA 109, 129594v & Formula Index 109, p. 2453F (1988).
Reed et al., "Haloakyldihydroxyoxahexy, etc.", CA, 63 P12945f, 1965.
Lacoste, "Hydrocarbylthiophosphonates and Lubricant, etc.", CA, 66, 48106d, 1967.

Primary Examiner—Glennon H. Hollrah
Attorney, Agent, or Firm—Walter Katz; Paul J. Juettner

[57] ABSTRACT

What is provided herein are new and useful surfactants characterized by having a large number of hydroxyl hydrophilic groups therein with the formula:

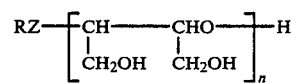

where
R is a long chain alkyl group,
Z is O or —NH, and
n=1–4.

3 Claims, No Drawings

SURFACTANT PRODUCTS CONTAINING 1,3,4-BUTANETRIOL

BACKGROUND OF THE INVENTION

1. Field of the Invention

This invention relates to surfactants, and more particularly, to surfactants having a predetermined number of hydrophilic groups.

2. Description of the Prior Art

Surfactants are compounds which contain both a hydrophobic portion and a hydrophilic (lipophilic) moiety. Often, the hydrophobic portion of the molecule consists of a long chain hydrocarbon unit, for example, $C_8$–$C_{22}$. The hydrophilic portion can consist of either an ionic or somewhat polar non-ionic grouping.

U.S. Pat. No. 2,833,788 describes the preparation of 2,3-epoxy-1,4-butanediol; however, this compound was not utilized for the preparation of surfactants.

Accordingly, it is an object of the present invention to provide new and improved surfactant compounds.

A more particular object herein is to provide surfactants having a hydrophobic portion and a predetermined number of hydrophilic groups, thus providing a surfactant with a desirable hydrophobic to lipophilic balance.

A specific object herein is to provide surfactant compounds containing 1,3,4-butanetriol.

These and other objects and features of the invention will be made apparent from the following description of the invention.

SUMMARY OF THE INVENTION

What is provided herein are new and useful surfactants characterized by having a large number of hydroxyl hydrophilic groups therein with the formula:

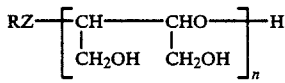

where
R is a long chain alkyl group,
Z is O or —NH, and
N=1–4.

Typical surfactant compounds of the invention include:

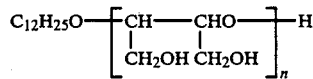

2-dodecyloxy-1,3,4-butanetriol; and

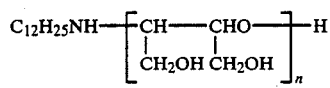

2-dodecylamino-1,3,4-butanetriol.

The compounds of the invention thus are surfactants which include a hydrophobic group (R) and several hydrophilic groups (three —OH and one —O). The presence of the large number of hydrophilic groups in the molecule provides an effective surfactant for use in commercial application.

DETAILED DESCRIPTION OF THE INVENTION

The surfactant compounds of the invention are made from 2,3-epoxy-1,4-butanediol by the following reactions:
where Z is —O—:

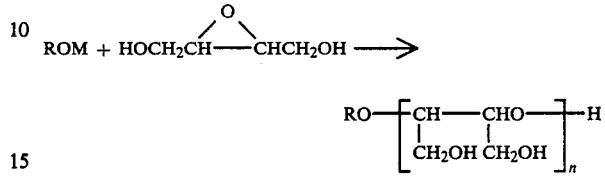

where Z is —NH—:

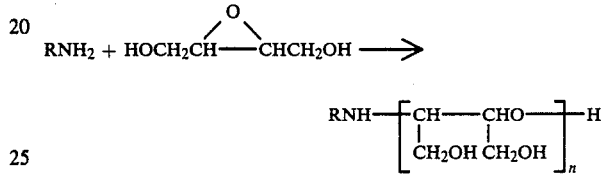

where R is a long chain alkyl radical, e.g. $C_8$–$C_{24}$ alkyl; M is an alkali metal such as sodium, potassium, etc.; and n is 1–4, preferably about 1.6.

The surfactant compounds of the invention are characterized by the presence of a hydrophobic group which is a long chain alkyl group and an unusual hydrophilic moiety, namely, three hydroxy groups and one oxy or amino group. This combination provides surfactant properties for these compounds consistent with the selected n number in the molecule. This number is determined by the ratio of starting materials used during reaction formation. Accordingly, compounds having a wide range of surfactant values can be provided herein for use in many different applications, including emulsifiers, wetting agents, detergents and solubilizers.

EXAMPLE 1

Preparation of 2-Dodecyloxy-1,3,4-Butanetriol

A. $C_{12}H_{25}ONa$

A 500 ml round bottom flask equipped with a condenser, thermometer (with controller) and overhead stirrer was charged with 93 g (0.5 moles) of $C_{12}H_{25}OH$ and (0.25 moles) of NaH. The mixture exothermed to 70° C. After the exotherm began to subside, the mixture was heated to 100° C. with stirring. After about two hours, a light grey paste was formed. This paste was subjected to a Kugelrohr distillation at 180° C. The non-volatile residue was 54.6% of the charge (theory for $C_{12}H_{24}ONa = 53.0\%$). The hard, dry, white powder residue was recovered. Analysis by titration showed the yield was 96.5% of theory for the named compound.

B. 2,3-Epoxy-1,4-Butanediol

This named starting material was prepared according to U.S. Pat. No. 2,833,788 by epoxidation of 2-butenediol with hydrogen peroxide; it was obtained as a white crystalline solid.

C. Reaction Process

A 500 ml round bottom flask equipped with a condenser, thermometer (with controller), and overhead stirrer was charged with
20.8 g (0.1 mole) $C_{12}H_{25}ONa$ 93.0 g (0.5 mole) $C_{12}H_{25}OH$ 50 g $CH_3OCH_2CH_2OCH_3$ (Glyme)

The mixture was stirred at 100° C. for 2 hours to give a hazy brown solution. Then 10.4 g (0.1 mole) of 2,3-epoxy-1,4-butanediol dissolved in 150 ml of $CH_3OCH_2CH_2OCH_3$ was added. The temperature of the reaction mixture was maintained at 100° C. for an additional 2-3 hours, cooled to room temperature and held there for an overnight period. A first precipitate product settled out of the mixture and was separated by filtration to yield 33.8 g of product. The filtrate was cooled to 0° C. to provide 45.5 g of a second precipitate. The remaining filtrate (63.8 g) was subjected to Kugelrohr distillation to give 1.2 g of a brown non-volatile semi-solid polymer.

The first and second precipitates were dissolved in methanol and acidified with HCl. Kugelrohr removal of the methanol produced a brown solid (10.8 g) which dissolved in $CHCl_3$ and had an NMR consistent with:

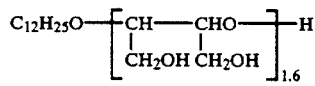

EXAMPLE 2

Preparation of 2-Dodecylamino-1,3,4-Butanetriol

Dodecylamine (185 g, 1.0 mole) was charged into a 500 ml round bottom flask equipped with a stirrer, thermometer (with temperature controller) and powder dropping funnel. Then 2,3-epoxy-1,4 butandiol (26 g, 0.4 moles) was placed in the dropping funnel. The mixture was stirred and heated while epoxide was being added so that suitable dissolution and reaction could occur. Upon completion of such addition the temperature of the reaction mixture was 100° C. The resulting mixture was stirred for 3 hours at 100° C. and distilled with a molecular still at 125° C. and <1 mm to remove excess dodecylamine. The resultant non-volatile product was cooled to give a light tan solid whose IR and NMR spectra were consistent with the formula

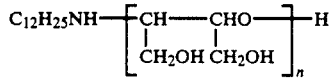

where
n=1.

EXAMPLE 3

The surfactants of Examples 1 and 2 were tested for lime soap dispersant properties, water solubility and complexation capability, and were found to be very effective in respect to these criteria for new and useful surfactant materials for commercial application.

While the invention has been described with particular reference to certain embodiments thereof, it will be understood that changes and modifications may be made which are within the skill of the art. Accordingly, it is intended to be bound only by the appended claims.

What is claimed is:

1. A surfactant product having the formula:

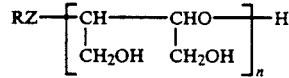

where

R is $C_8$-$C_{24}$ alkyl;

Z is —O—; and n is greater than 1 and up to 4, which is prepared by reaction of 2,3-epoxy-1,4-butanediol with ROM, where M is an alkali metal.

2. A surfactant product according to claim 1 wherein n is about 1.6.

3. A surfactant product according to claim 2 which is a 2-dodecyloxy-1,3,4-butanetriol.

* * * * *